(12) United States Patent
Radzinsky

(10) Patent No.: US 9,155,635 B2
(45) Date of Patent: Oct. 13, 2015

(54) CLAMPS FOR PROSTHETIC LIMBS AND METHODS OF MAKING CLAMPS FOR PROSTHETIC LIMBS

(71) Applicant: Vladimir Radzinsky, Beverly Hills, CA (US)

(72) Inventor: Vladimir Radzinsky, Beverly Hills, CA (US)

(*) Notice: Subject to any disclaimer, the term of this patent is extended or adjusted under 35 U.S.C. 154(b) by 0 days.

(21) Appl. No.: 14/162,087

(22) Filed: Jan. 23, 2014

(65) Prior Publication Data
US 2015/0202058 A1     Jul. 23, 2015

(51) Int. Cl.
*A61F 2/50* (2006.01)
*A61F 2/76* (2006.01)

(52) U.S. Cl.
CPC ............. *A61F 2/76* (2013.01); *A61F 2002/509* (2013.01); *A61F 2002/5016* (2013.01); *A61F 2002/5018* (2013.01); *A61F 2002/5083* (2013.01)

(58) Field of Classification Search
CPC ............... A61F 2/60; A61F 2/76; A61F 2/66; A61F 2002/5012; A61F 2002/5016; A61F 2002/5018; A61F 2002/502; A61F 2002/5021; A61F 2002/5023; A61F 2002/5024; A61F 2002/5027; A61F 2002/5029; A61F 2002/5081; A61F 2002/5083; A61F 2002/5084; A61F 2002/509; A61F 2002/607
USPC .................................... 623/27–38, 53, 57, 65
See application file for complete search history.

(56) References Cited

U.S. PATENT DOCUMENTS

| | | | | |
|---|---|---|---|---|
| 1,617,925 | A * | 2/1927 | Shrodes | 623/52 |
| 5,571,211 | A * | 11/1996 | Hiemisch et al. | 623/38 |
| 5,653,768 | A * | 8/1997 | Kania | 623/55 |
| 5,779,735 | A * | 7/1998 | Molino | 623/44 |
| 5,888,232 | A * | 3/1999 | Taylor | 623/38 |
| 7,033,400 | B2 * | 4/2006 | Currier | 623/33 |
| 2005/0049720 | A1 * | 3/2005 | Benson | 623/38 |
| 2008/0298886 | A1 * | 12/2008 | Chen | 403/373 |
| 2012/0018594 | A1 | 1/2012 | Radzinsky | |

FOREIGN PATENT DOCUMENTS

| | | | | |
|---|---|---|---|---|
| DE | 10027760 A1 * | 12/2001 | | A61F 2/76 |
| EP | 267347 A1 * | 5/1988 | | A61F 2/76 |
| EP | 0976370 A1 * | 5/2000 | | A61F 2/60 |

OTHER PUBLICATIONS

Medi Clever Bones (1, 2 are different views). Verified by the wayback machine Jul. 20, 2013.*
English translation of EP0976370 from Espacenet.*
Angarami, Geraldo. An Efficient Low Cost Prosthetic Structural System. Journal of Prosthetics and Orthotics. 1998. vol. 1, No. 2, 86-91.*
Medi Clever Bones. Medi Product Website.*

(Continued)

*Primary Examiner* — Thomas J Sweet
*Assistant Examiner* — Christie Bahena
(74) *Attorney, Agent, or Firm* — Fulwider Patton LLP

(57) ABSTRACT

A clamp for a prosthetic limb includes a first section configured to couple to a first portion of a prosthetic limb and a second section being separate and spaced apart from the first section and configured to couple to a second portion of a prosthetic limb. The clamp further includes a plurality of pins extending between the first section and the second section and connecting the first section to the second section, each pin having a first end connected to the first section and a second end opposite to the first end and connected to the second section.

14 Claims, 18 Drawing Sheets

(56) References Cited

OTHER PUBLICATIONS

Edwards, Mark. Solutions for the Prosthetic Fitting of Bariatric Patients Using Ottobock Components. The Academy Today. Jan. 2013.*

Materials Background. Composite Theory. MIT Website.*
Young's Modulus. (Young's modulus is a measure of stiffness).*
Derwent Abstract of SU564862. Kondrashin. Aug. 22, 1977.*
BP3 Neuropsychogenic by Dycor Manufacturing. http://www.dycormfg.com/newprods.html, Accessed on: Jan. 23, 2014.

* cited by examiner

CLAMPS FOR PROSTHETIC LIMBS AND METHODS OF MAKING CLAMPS FOR PROSTHETIC LIMBS

FIELD

The present disclosure relates generally to prosthetic limbs, and more particularly, to clamps for prosthetic limbs and methods of making clamps for prosthetic limbs.

BACKGROUND

Prosthetic limbs are attached to a residual limb or stump of an amputee by a stump socket, which is a shell that closely conforms to the residual limb. For example, a knee prosthetic includes a stump socket that is attached to the stump of an amputee. The stump socket has a threaded socket adaptor which is adapted to engage with an intermediate connector, such a pyramid plug. The pyramid plug then connects the socket adaptor to an upper tube clamp. A lower tube clamp is connected to the upper tube clamp with a tube. The lower tube clamp is then connected to a prosthetic foot with a connector.

DESCRIPTION

Figure 1:
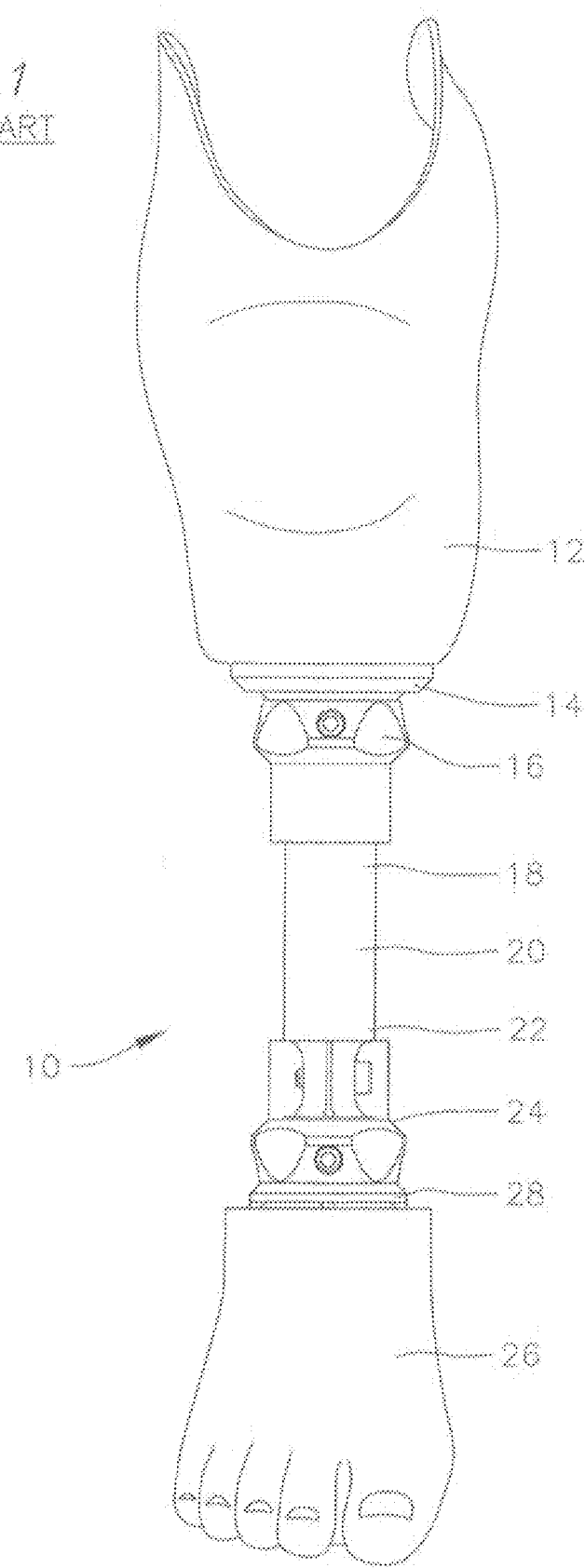
FIG. 1 shows a prior art below the knee prosthetic.
Figure 3:
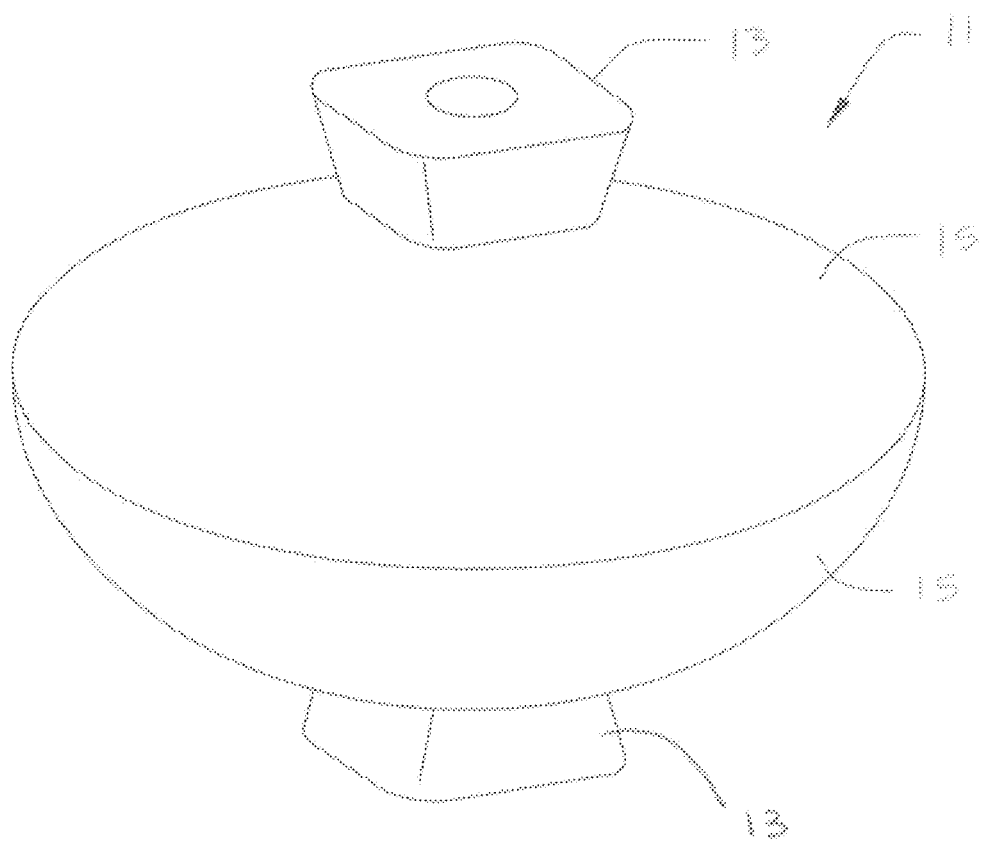
FIG. 3 is a prior arts pyramid plug for use with the tube clamp of a prosthetic limb.

FIG. 1 shows a typical below the knee prosthetic 10. A residual limb or stump socket 12 fits onto the residual limb (not shown) of a patient. The stump socket 12 has a socket adaptor 14 at a lower end, and is adapted to engage with an intermediate connector, such a pyramid plug 11 (shown in FIG. 3) or any prosthetic part having a male pyramid. The pyramid plug 11 connects the socket adaptor 14 to a receiver 16, which is fitted on a first end 18 of a tube 20. At the second end 22 of the tube 20 a tube clamp 24 is attached. The tube clamp 24 is in turn connected to a prosthetic foot 26 with a connector 28. The receiver 16 and the clamp 24 may be the same part.

Figure 2:
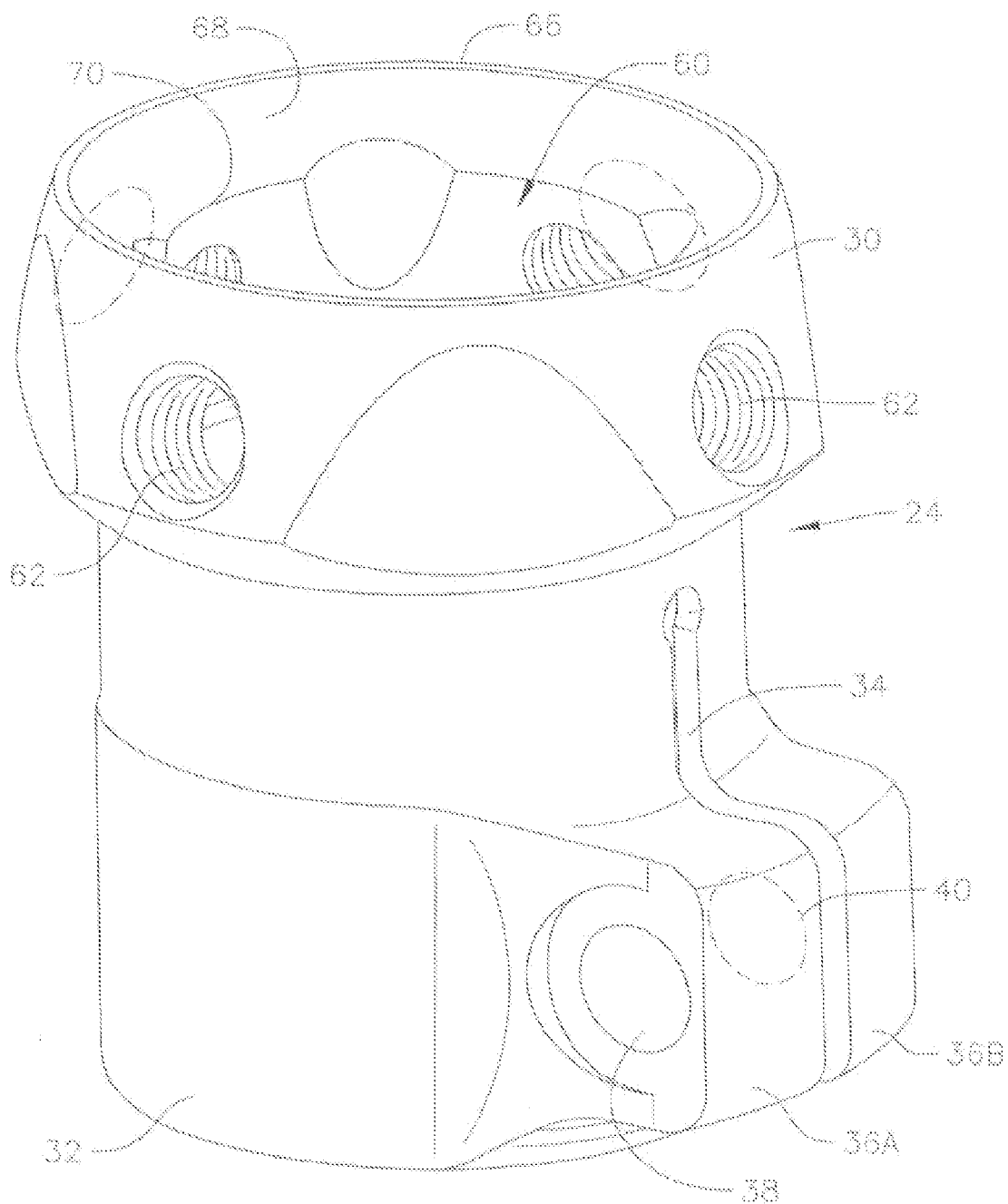
FIG. 2 is a prior art tube clamp for a prosthetic limb.

FIG. 2 shows a detailed view of the tube clamp 24, which has a frustum receiving head region 30, and a clamping portion 32. A slot 34 is formed through the sidewall 48 of the clamping portion 32 and extends between two ears 36A and 36B. A bolt (not shown) can pass through an enlarged hole 38 in ear 36A and be threaded into ear 36B which has a threaded hole 40. The tube clamp 24 is cylindrical so as to define a bore 60. The tube 20 can be received in the bore 60 and secured in the bore by tightening the bolt, i.e., moving the ears 36A and 36B toward each other.

Four threaded holes 62 are formed through a perimeter of the head region 30. The threaded holes 62 are tilted downwardly and are adapted to receive bolts (not shown) which can project into the bore 60. The bolts engage and hold a frustum head 13 of the pyramid plug 11 within the bore 60. The head region 30 has a top end 66 at the entrance of the bore 60. A cupped rim 68 is formed at the top end 66 of the bore 60 and narrows in a direction inside the bore 60. The cupped rim 68 is adapted to act as a seat for a spheroidal base region 15 of the pyramid plug 11 and allows the pyramid plug 11 to be swiveled relative to the tube clamp 24. After the pyramid plug 11 is received in the bore 60 and the position thereof is adjusted, the bolts/screws that are in the bores 60 are tightened to secure the pyramid plug 11 in the bore 60.

Figure 4:
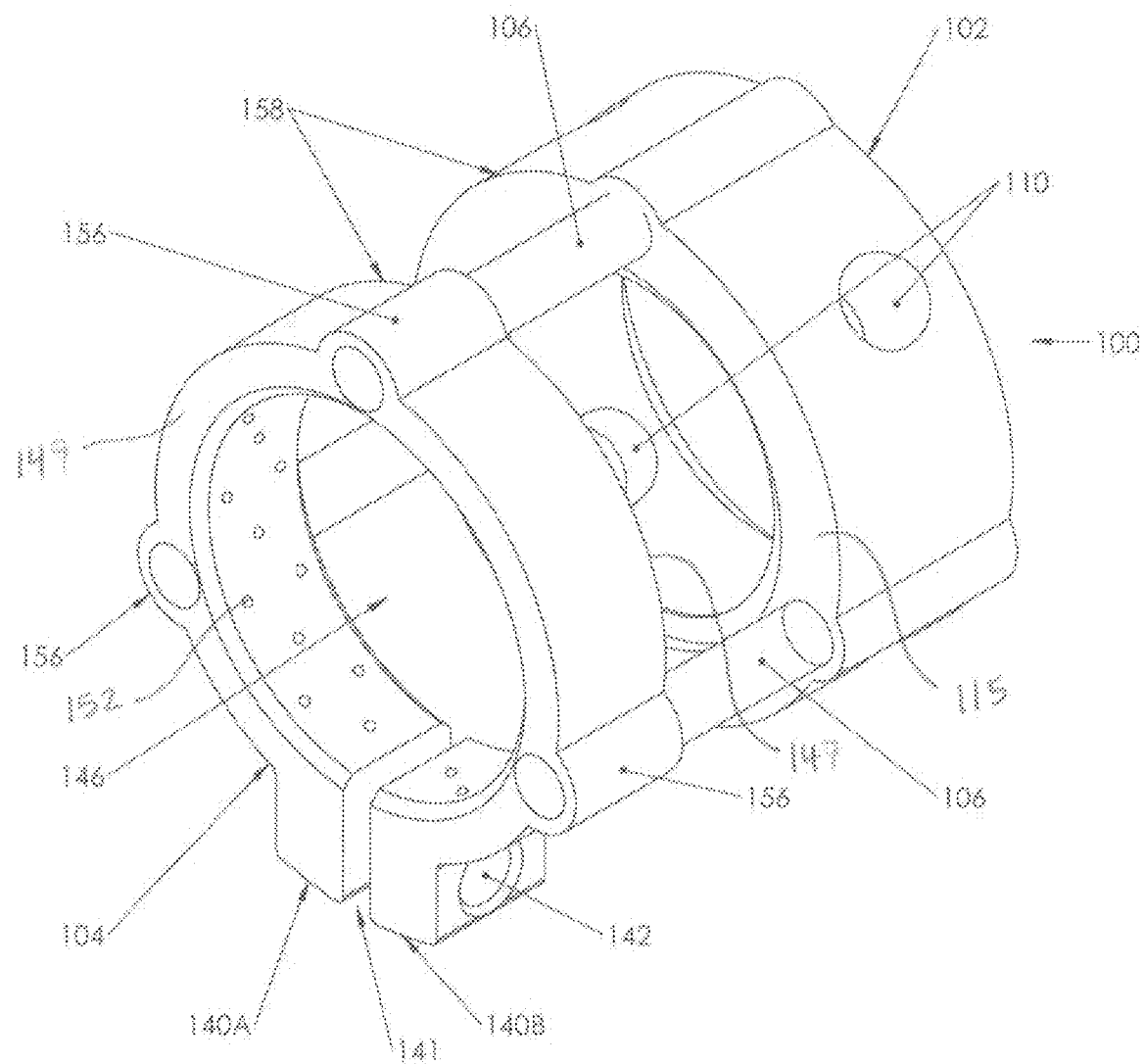
FIG. 4 is a perspective view of a clamp for prosthetics limbs according to one embodiment.
Figure 5:
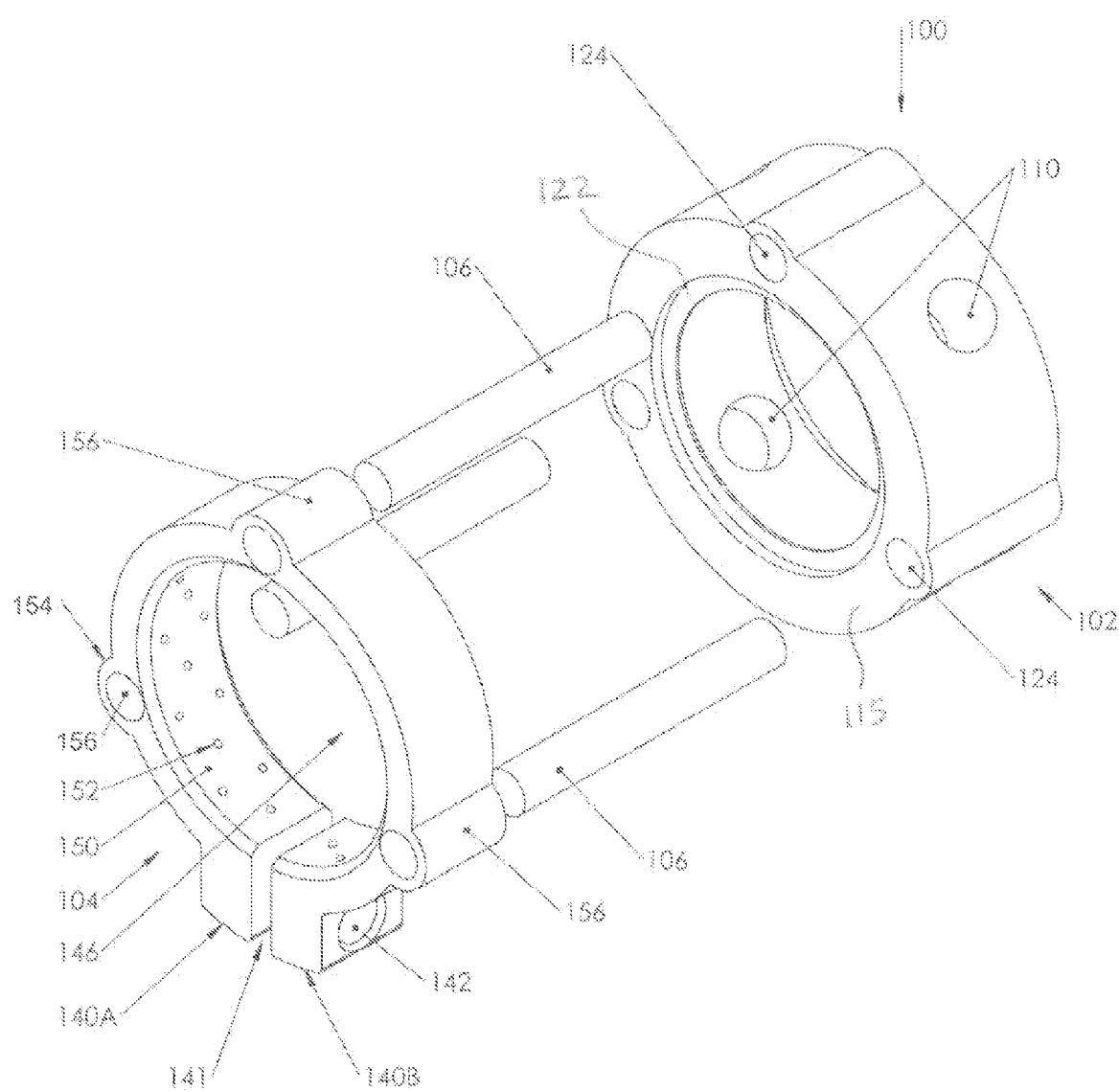
FIG. 5 is an exploded perspective view of the clamp of FIG. 4.
Figure 6:
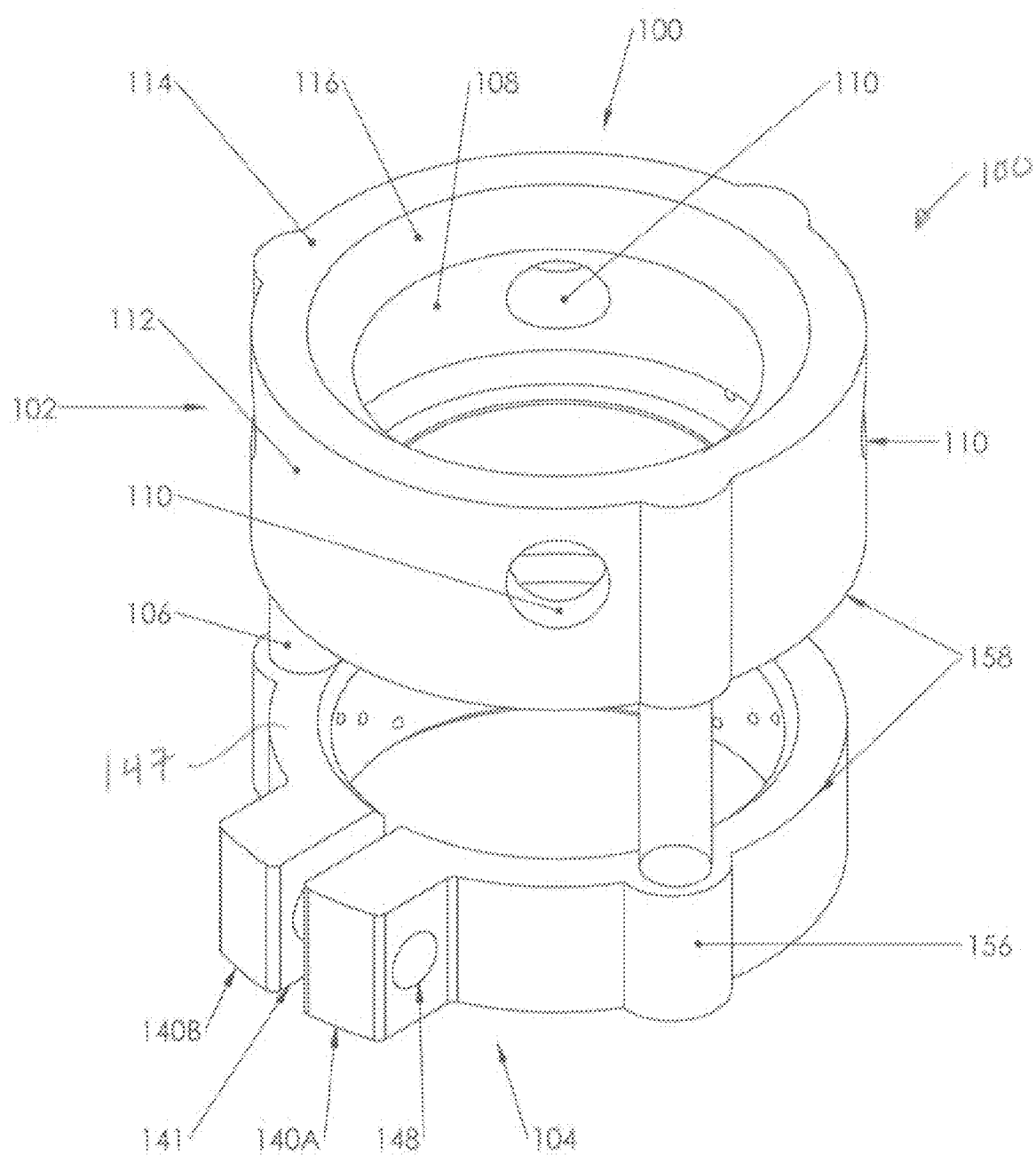
FIG. 6 is another perspective view of the clamp of FIG. 4.
Figure 7:
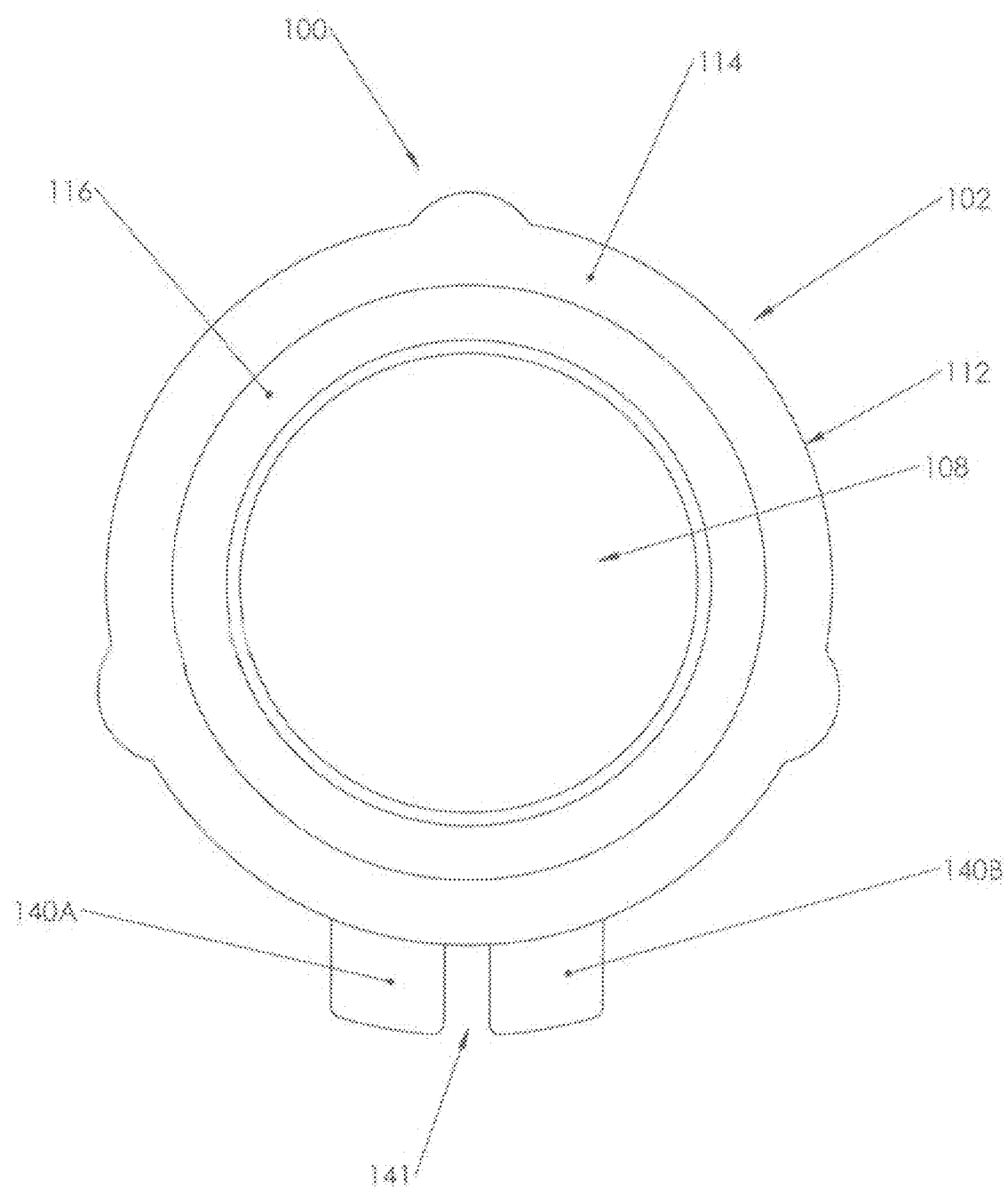
FIG. 7 is a top view of the clamp of FIG. 4.
Figure 8:
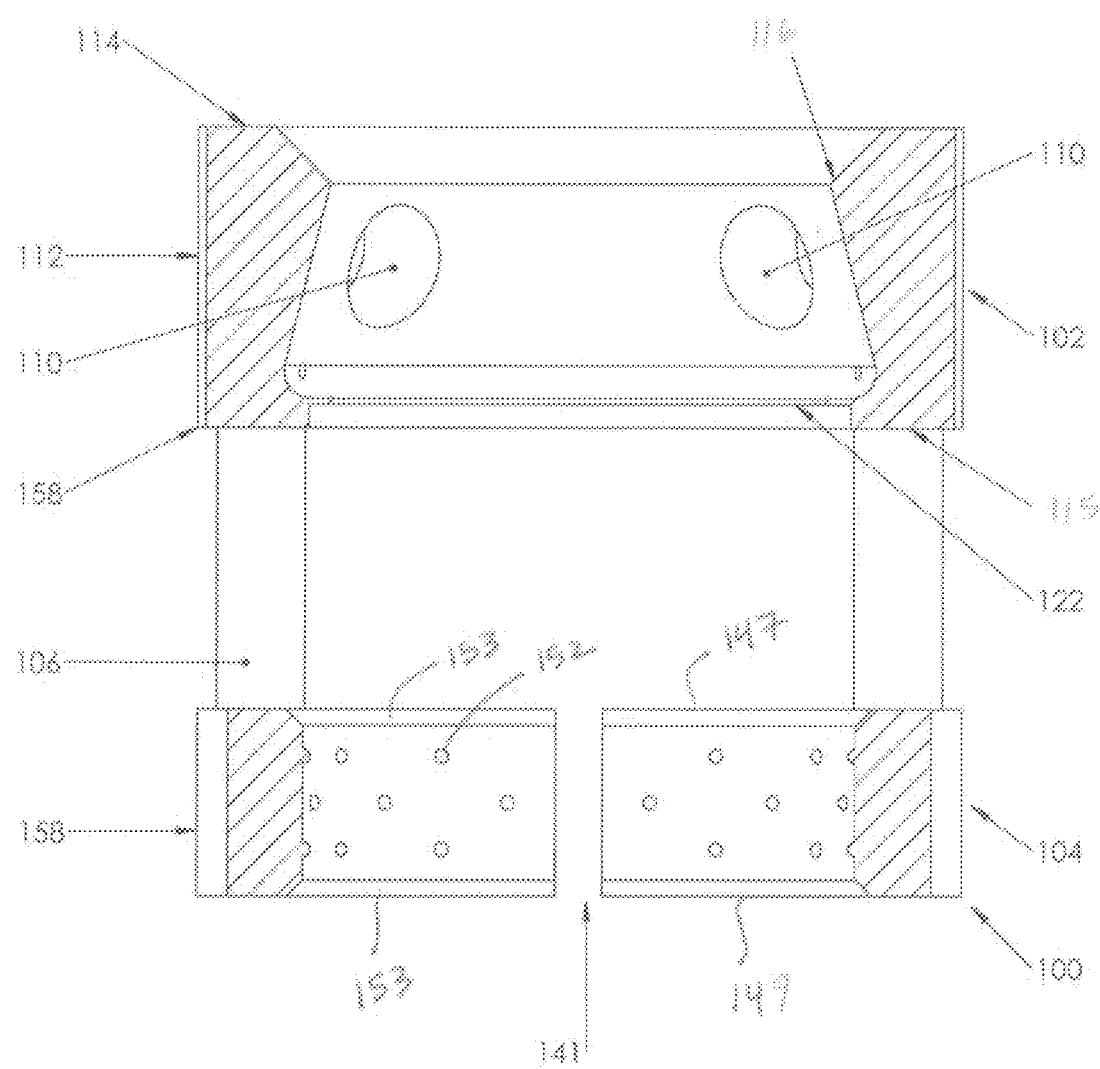
FIG. 8 is a cross-sectional view of the clamp of FIG. 4.
Figure 9:
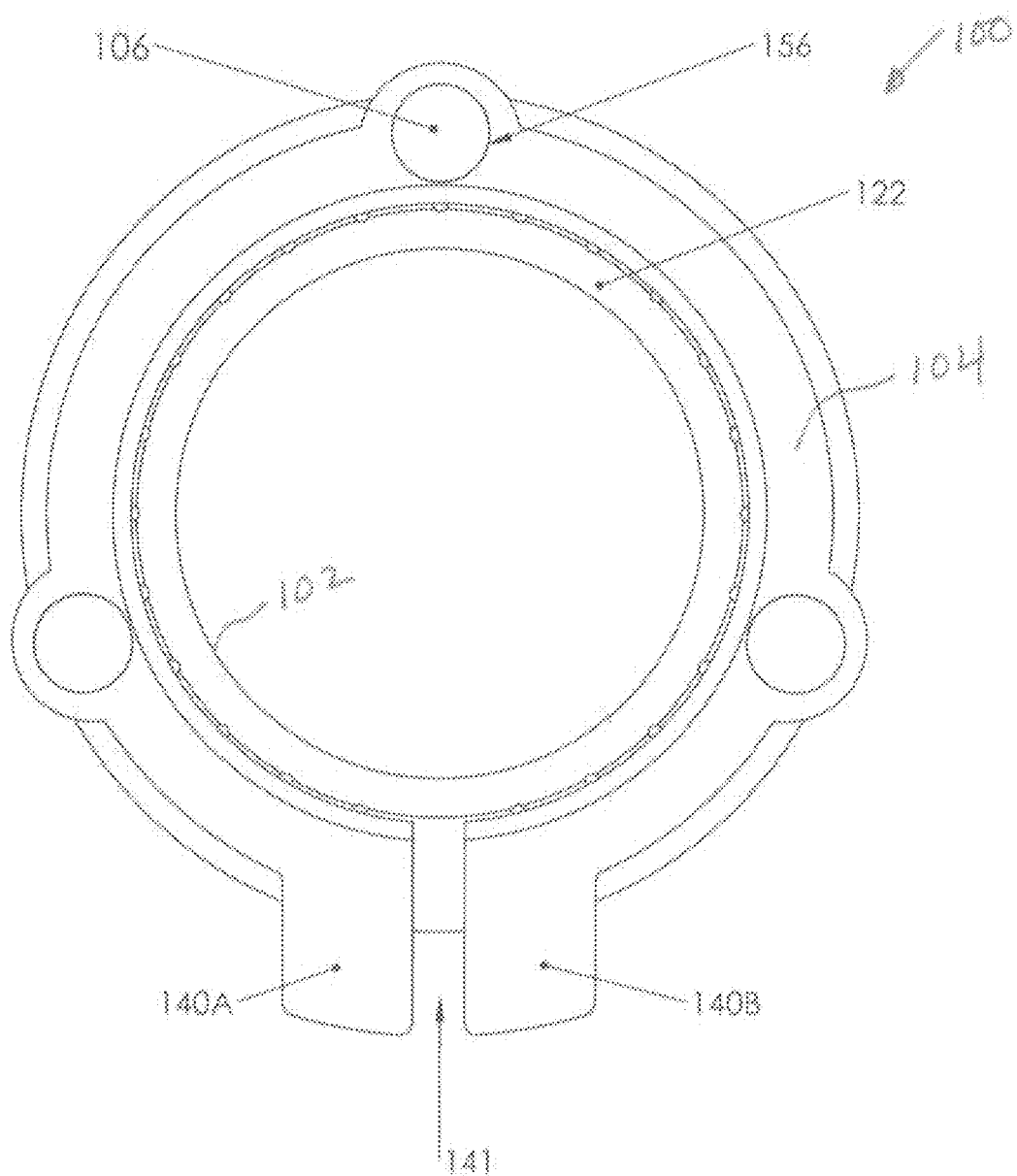
FIG. 9 is a bottom view of the clamp of FIG. 4.

FIGS. 4-6 show a clamp 100 according to one embodiment. The clamp 100 includes a head section 102, a clamp section 104 and a plurality of pins 106 that connect the head section 102 to the clamp section 104. The head section 102 may be generally cylindrical and may be constructed from two or more sections/parts 158 as described below for receiving a pyramid plug similar to the pyramid plug 11. A first end 114 (shown in FIG. 6) of the head section 102 may include a cupped rim 116 that extends from the first end 114 and narrows in a direction toward the center of the bore 108 as shown in FIG. 8. Below the cupped rim 116, the inner wall of the bore 108 extends outwardly so as to accommodate the frustum 13 of the pyramid plug 11. Thus, the bore 108 narrows from the first end 114 to define the cupped rim 116 and then expands to the second end 115. Additionally, the bore 108 includes an enlarged diameter section at the second end 115 that defines a stop or ledge 122. When a tube or pylon such as the tube 20 is received in the clamp 100 from the direction of the clamp section 104, the tube engages the ledge 122 to prevent further insertion of the tube into the bore 108.

The cupped rim 116 is adapted to function as a seat for the base region 15 of the pyramid plug 11 and allows the pyramid plug 11 to swivel relative to the clamp 100. Threaded holes 110 may be formed through a perimeter 112 of the clamp 100. Each of the threaded holes 110 may be tilted downwardly and adapted to receive a bolt/screw (not shown) which can project into the bore 108. After the pyramid plug 11 is received in the bore 108 and the position thereof is adjusted, the bolts/screws that are in the bores 108 can be tightened to secure the pyramid plug 11 in the bore 108 in a preferred swiveled position. The head section 102 also includes a plurality of axial bores 124 that extend from the first end 114 toward the second end 115 of the head section 102. The axial bores 124 may be blind bores that have an opening at the first end 114. Alternatively, the axial bores 124 may be through bores. The thickness of the head section 102 may be sufficient to accommodate the axial bores 124. However, as shown in the example of FIG. 5, portions of the head section 102 that include the axial bores 124 may have a greater thickness and/or outer diameter to accommodate the axial bores 124. Each of the axial bores 124 is configured to receive one of the pins 106 as described in detail below.

The clamp section 104 may be generally cylindrical 158 to define a bore 146. The clamp section 104 includes a plurality of axial bores 156 that extend from a first end 147 toward a second end 149 of the clamp section and are configured to receive the pins 106 as described below. In the example shown, the clamp 100 includes 3 pins that are about 120° apart. However any number of pins with any angular arrangement may be used. The pins may be manufactured from titanium, titanium alloys, steel or other high strength materials. The axial bores 156 may be blind bores that have an opening at the first end 147. Alternatively, the axial bores 156 may be through bores. The thickness of the clamp section 104 may be sufficient to accommodate the axial bores 156. However, as shown in the example of FIG. 4, portions 154 of the clamp section 104 that include the axial bores 156 may have a greater thickness and/or outer diameter to accommodate the axial bores 156.

The clamp section 104 includes a break or a gap 141 defined by a first clamp ear 140A and a second clamp ear 140B. The clamp ear 140B includes a bore 142 for receiving a bolt (not shown). The clamp ear 140A includes a threaded bore 143 for receiving the bolt. When the bolt is inserted into the bore 142 and threaded into the threaded bore 143 of the clamp ear 140A, the two ears 140A and 140B are pulled toward each other to reduce the diameter of the bore 146 of the clamp section 104. Conversely, loosening the bolt causes the gap 141 to expand to increase the diameter of the bore 146 of the clamp section 104 to the rest condition. Each of the clamp ears 140A and 140B define an angle of about 3° relative to vertical at rest so that when the bolt is fastened through the clamp ears and the gap 141 shrinks, each of the clamp ears formed an angle of about 0° with the vertical.

Figure 10:
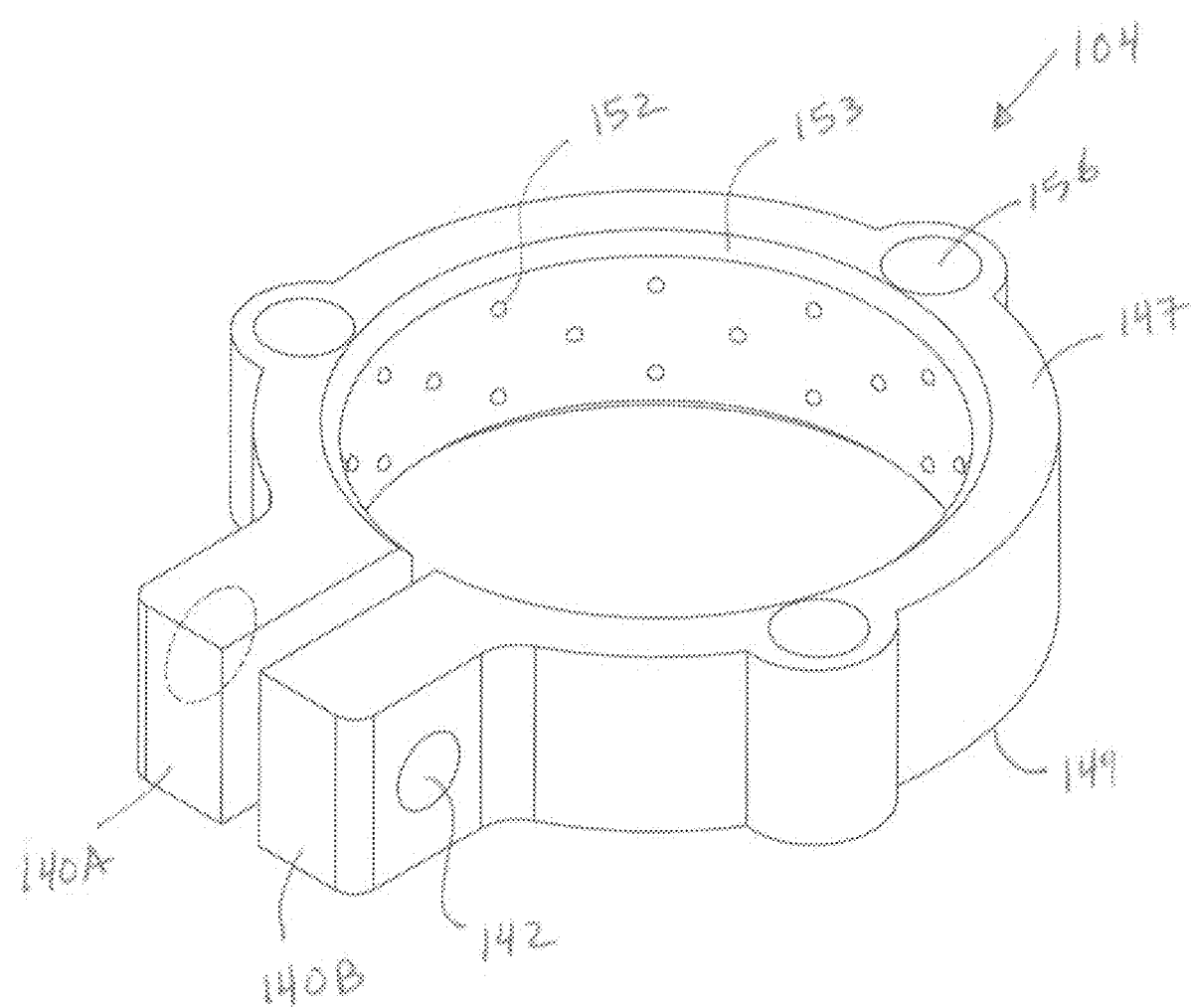
FIG. 10 is a perspective view of the clamp section of the clamp of FIG. 4.

The diameter of the bore 146 is configured to receive a tube such as the tube 20 of FIG. 1. The inner wall 150 of the clamp section 104 may include projections 152 to enhance the grip between the inner wall 150 and the tube when the gap 141 is reduced to lock the tube in engagement with the clamp section 104. However, other grip or friction enhancing structures such as knurls may be provided on the inner wall 150 of the clamp section 104. Referring to FIGS. 8 and 10, the clamp section 104 may include cupped rims 153 at both ends 147 and 149 to assist and provide guidance for the tube when the tube is inserted into the bore 146. As shown in FIG. 10, the clamp section 104 may be symmetrical with respect to a plane that is perpendicular to the axis of the bore 146. Accordingly, the clamp section 104 may be positioned on the clamp 100 from either the first side 147 or the second side 149.

Figure 11:
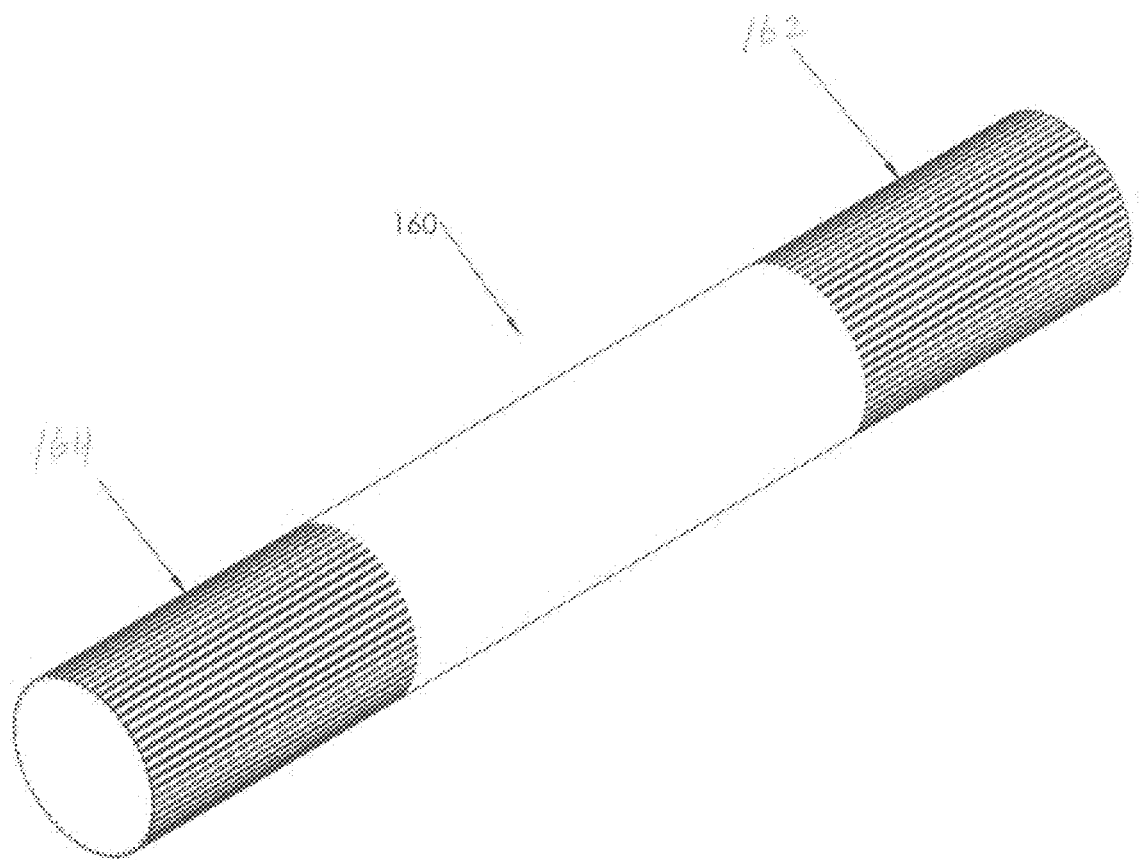
FIG. 11 is a perspective view of a pin of the clamp of FIG. 4.

FIG. 11 shows a pin 160 according to one embodiment. The pin 160 includes a first end 162 and the second end 164. The first end 162 may be configured for connection to the bore 124 of the head section 102. The second end 164 may be configured for connection to the bore 156 of the clamp section 104. However, if the bore 124 and the bore 156 have the same diameters, the first end 162 and the second end 164 may be interchangeably received in the bores 124 or 156. According to the embodiment shown in FIG. 11, the first end 162 and the second end 164 have the same outer diameters. Accordingly, the diameters of the bores 124 and 156 may also be the same to interchangeably receive the first end 162 or the second end 164 of the pin 160. The first and 162 and the second end 164 may be connected to the bores 124 and 156 by any method such as with an adhesive, by welding, by soldering, with frictional engagement, or with fasteners. In the example of FIG. 11, the first end 162 and the second end 164 have knurled surfaces to provide for an interference fit of the pin 160 with the bores 124 and 156. Thus, the first end 162 and the second end 164 of the pin 160 may be forcibly inserted into the bores 124 and 156 and secured therein by the frictional engagement and the interference fit between the knurled surfaces of the first end 162 and the second end 164 and the bores 124 and 156.

Figure 12:
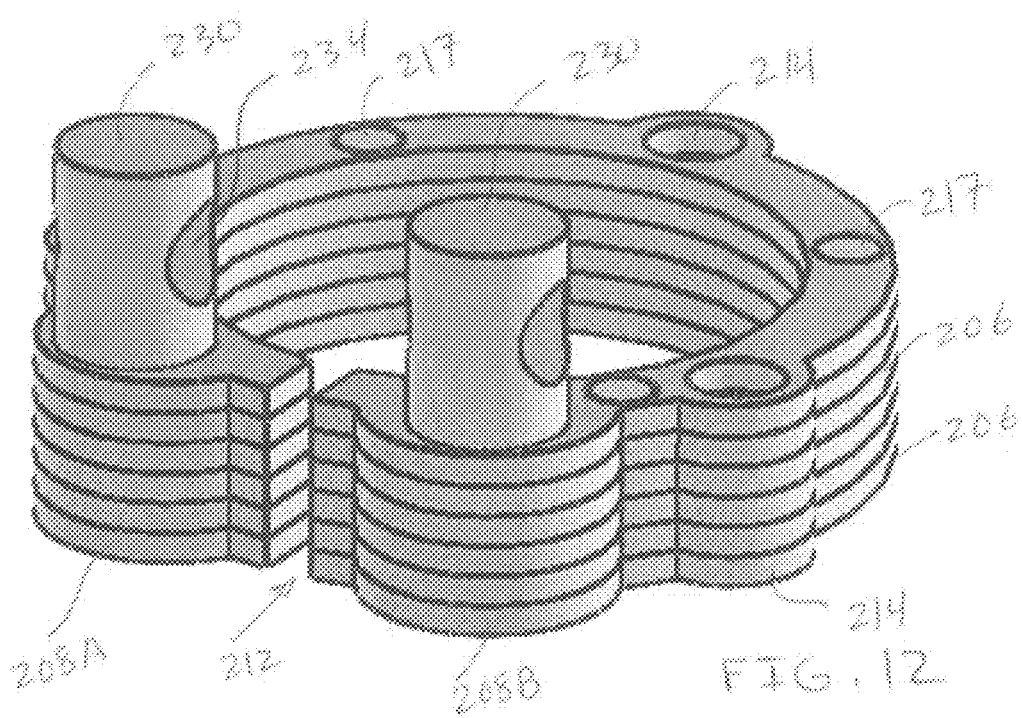
FIG. 12 is a perspective view of a clamp section of the clamp for a prosthetic limb according to one embodiment.
Figure 13:
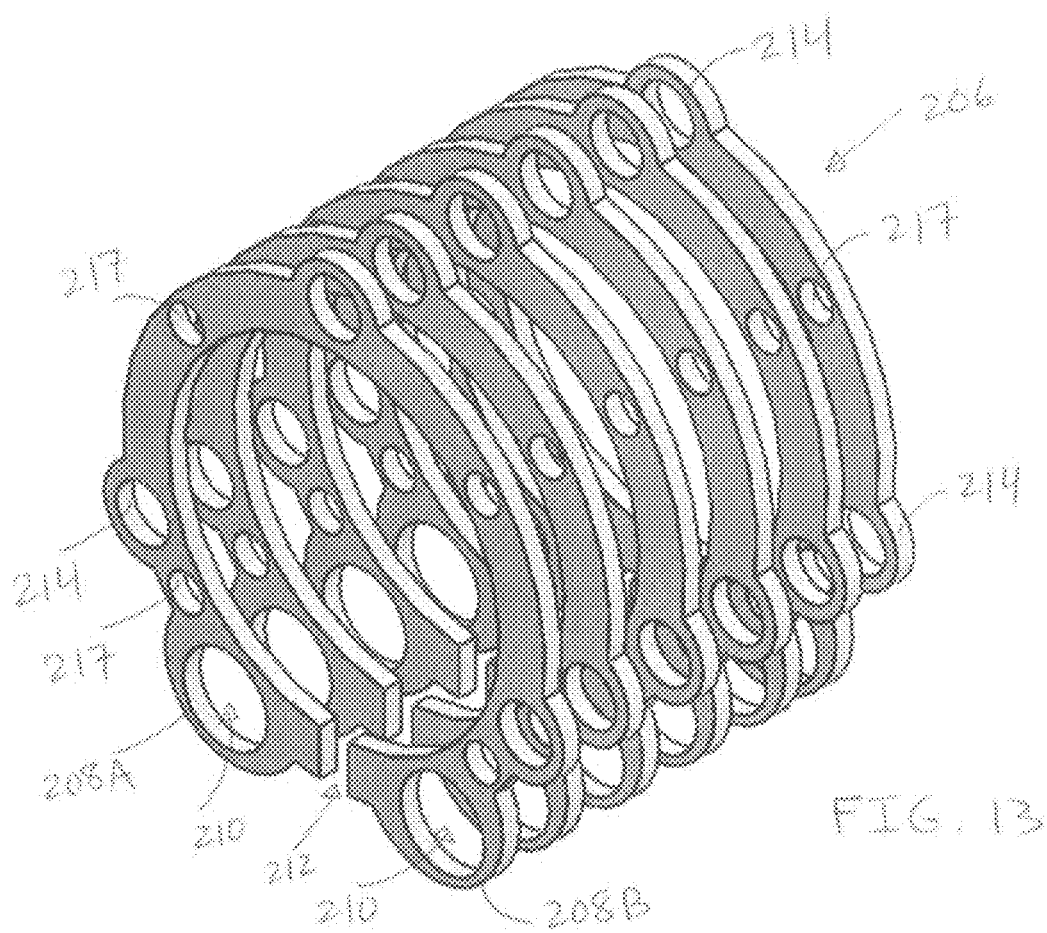
FIG. 13 some exploded perspective view of the clamp section of FIG. 12.
Figure 14:
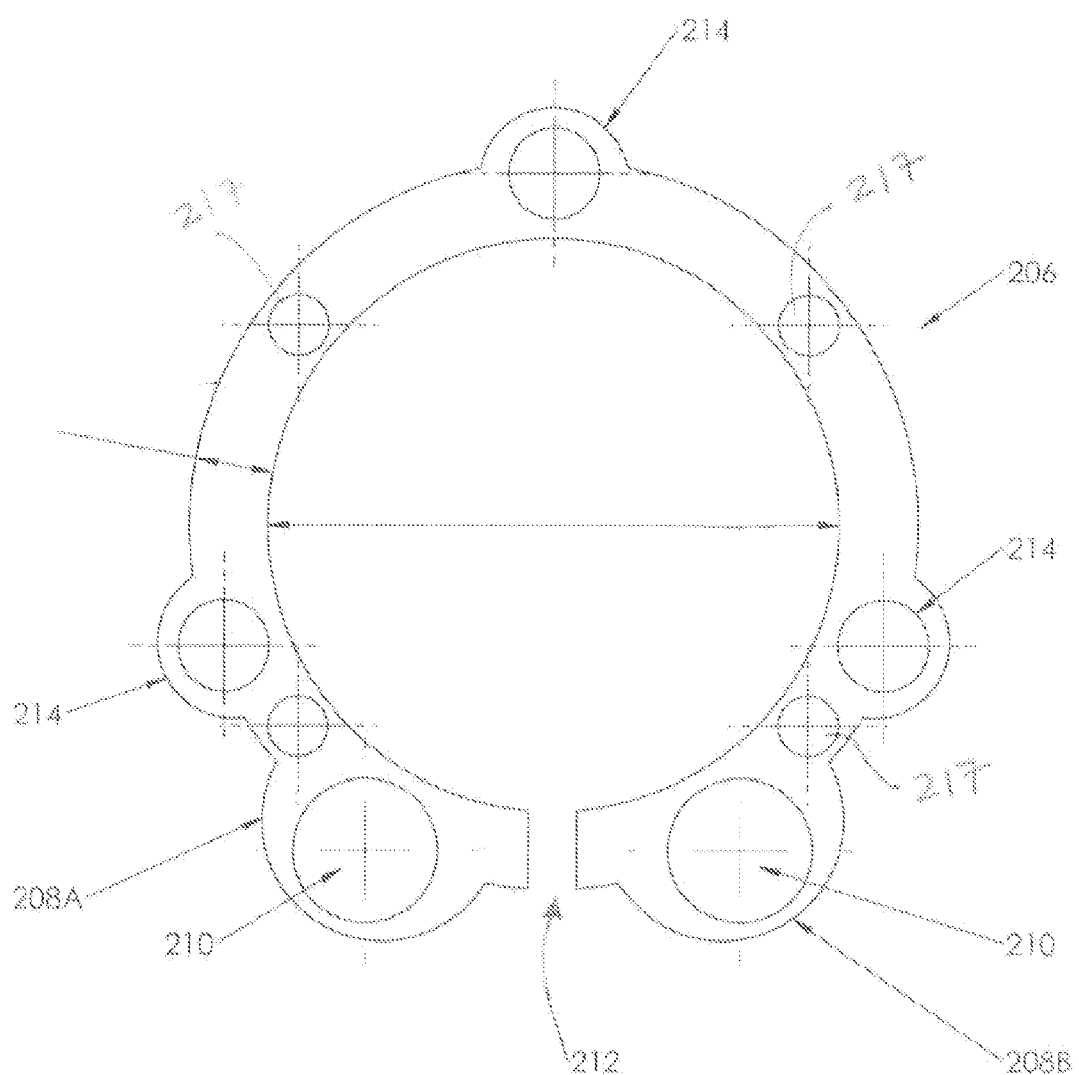
FIG. 14 is a top or bottom view of the clamp section of FIG. 12.

Referring to FIGS. 12-14, a clamping section 204 according to another embodiment is shown. The clamping section 204 includes a plurality of stacked disks 206 that maybe attached together by an adhesive, welding, soldering, fasteners and/or rivets. Referring to FIG. 14, each disc 206 includes a plurality of axial bores 214 for receiving pins 160. When the discs 206 are properly stacked on top of each other, the axial bores 214 are axially aligned so as to receive the first end 162 or the second end 164 of the pin 160. In the embodiment of FIGS. 12-14, each disc 206 also includes a plurality of axial bores 217 for receiving fasteners or rivets for securing the discs 206 together. Accordingly, when the discs 206 are properly stacked on top of each other, the axial bores 217 are axially aligned to receive a fastener or a rivet.

Figure 15:
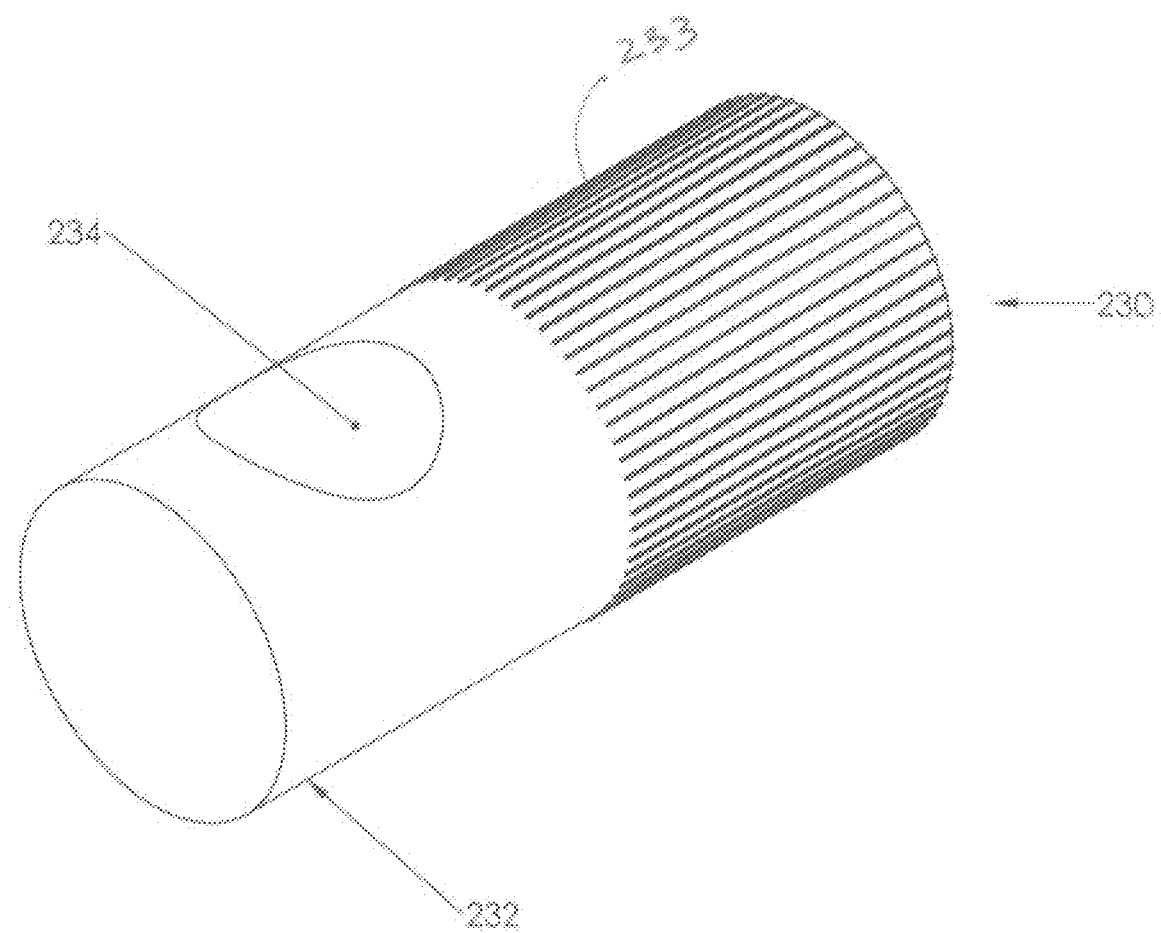
FIG. 15 is a perspective view of the pin for use with the clamp section of FIG. 12.

The clamp section 204 includes a break or a gap 212 defined by a first clamp ear 208A and a second clamp ear 208B. Each clamp ear may be defined by an enlarged section of the clamp section 204 and includes an axial bore 210. As shown in FIG. 14, the axial bores 210 may be larger than the axial bores 214 to accommodate a larger pin than the pin 160 as described in the following. Referring to FIG. 15, the clamp section 204 includes two pins 230. Each pin 230 includes a first end 232, a second end 233 and a bore 234 extending through the pin 230 transverse to the axis of the pin 230. As shown in FIG. 12, the first end 232 or the second end 233 is received in the axial bores 210 of the clamp ears 208A and 208B. The second end 233 may be knurled or have a frictionally enhanced surface to fit inside the axial bore 210 by an interference fit. Alternatively, the second end 233 may be secured inside the axial bore 210 with an adhesive, by welding, by soldering, with one or more fasteners or other methods. The two pins 230 are inserted into the axial bores 210 so that the transverse bores 234 of the pins 230 become generally coaxial. Accordingly, a fastener such as a bolt and nut combination may be inserted into the transverse bores 234. Tightening the nut on the bolt shrinks the gap 212 so that the clamp section 204 frictionally secures a tube, such as the tube 20 in the bore 146 (see FIG. 4) that is defined by the tube clamp 100. Alternatively, the bore 234 of one of the pins 230 may be threaded to receive a bolt such that a bolt and nut combination is not required.

The number of discs 206, the thickness and/or the materials of the clamp section 204 may vary to provide certain flexibility or stiffness and/or an overall thickness to the clamp section 204 depending on the application for which the clamp section 204 is used. For example, one or more of the discs may be constructed from titanium or titanium alloys, one or more of discs may be constructed from a carbon composite, and/or one or more of the discs may be constructed from aluminum or aluminum alloys. Furthermore, one or more of the discs may be constructed from a dampening material. Because the clamping section 204 is constructed from a plurality of discs, a crack in one disc cannot propagate through the remaining discs or the entire clamp 100. The plurality of discs better absorb loading, bending intention as compared to a one-piece part.

Figure 16:
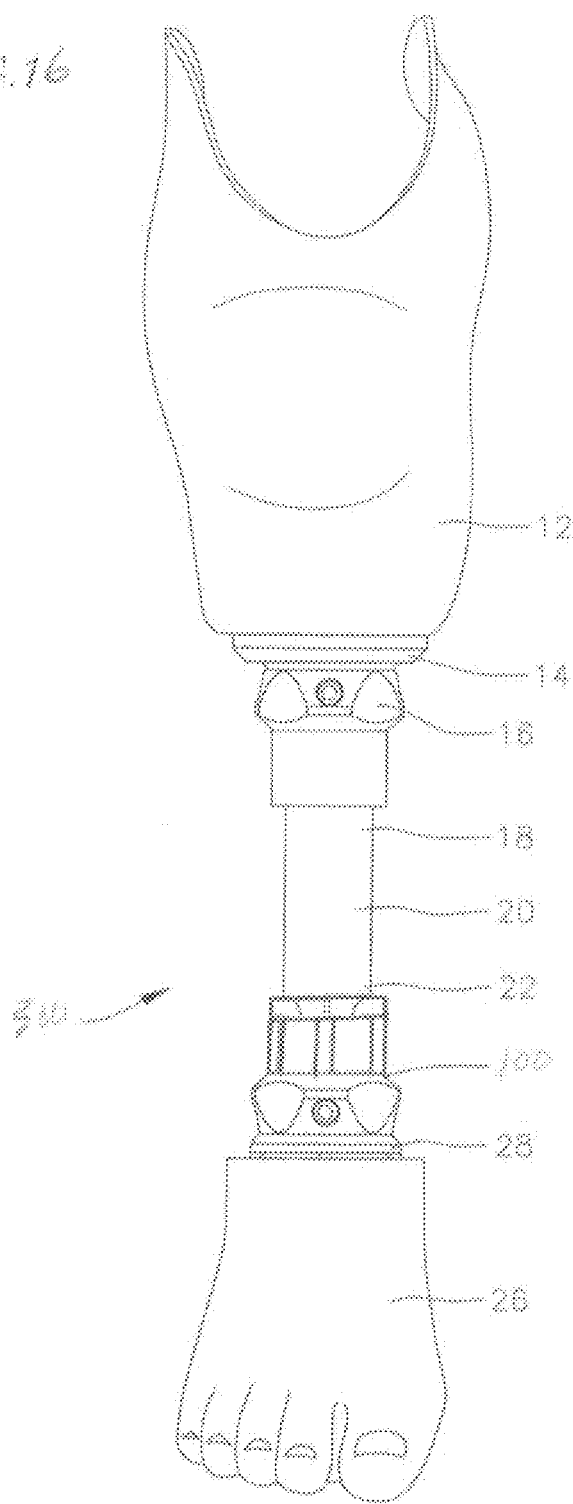
FIG. 16 is a prosthetic limb having a clamp according to one embodiment.

Referring to FIG. 16, a below the knee prosthetic 300 is shown. The prosthetic 300 is similar in many respects to the prosthetic 10 of FIG. 1. Accordingly, similar parts are referred to with the same reference numbers. The prosthetic 300 shows an application of the clamp 100 as described above. Similar to FIG. 1, a residual limb or stump socket 12 fits onto the residual limb (not shown) of a patient. The stump socket 12 has a socket adaptor 14 at a lower end, and is adapted to engage with an intermediate connector, such a pyramid plug 11 (shown in FIG. 3). The pyramid plug 11 connects the socket adaptor 14 to a receiver 16, which is fitted on a first end 18 of a tube 20. At the second end 22 of the tube 20, the clamp 100 is attached. The clamp 100 is in turn connected to a prosthetic foot 26 with a connector 28. Although not shown in FIG. 16, the receiver 16 and the clamp 100 may be the same part. In other words, a pair of clamps 100 may be used at both ends of the tube 20.

Figure 17:
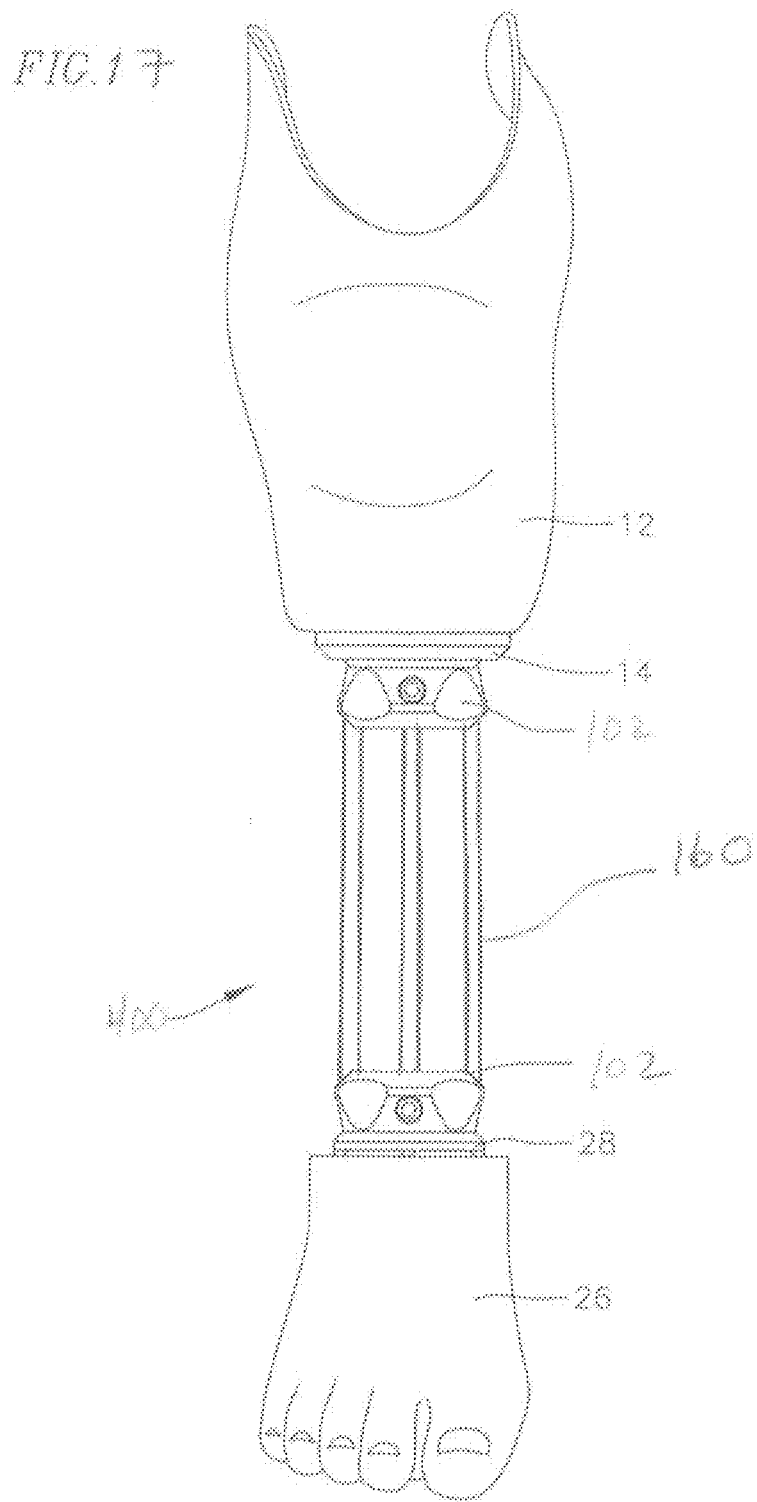
FIG. 17 is a prosthetic limb according to one embodiment.

FIG. 17 shows a below the knee prosthetic 400 according to another embodiment. The prosthetic 400 is similar in many respects to the prosthetic 10 of FIG. 1. Accordingly, similar parts are referred to with the same reference numbers. Similar to FIG. 1, a residual limb or stump socket 12 fits onto the residual limb (not shown) of a patient. The stump socket 12 has a socket adapter 14 at a lower end, and is adapted to engage with an intermediate connector, such as a pyramid plug 11 (shown in FIG. 3). The pyramid plug 11 connects to a head section 102 as described in detail above. However, the head section 102 is not connected to a clamp section 104 with pins 160. As shown in FIG. 17, the prosthetic 400 includes elongated pins 160 that are connected to another head section 102 at the lower portion of the prosthetic 400. The head section 102 is then connected to a prosthetic foot 26 with a connector 28. Accordingly, the elongated pins 160 replace the tube 20 and function as the connection between the upper portion and the lower portion of the prosthetic 400. The prosthetic 400 may provide easier length adjustability by allowing an individual to replace the pins 160 with shorter or longer pins. Furthermore, the prosthetic 400 may be lighter than a prosthetic having clamps and a tube as shown in FIG. 1. Additionally, the prosthetic 400 may be easier to assemble than the prosthetic of FIG. 1. Additionally yet, the prosthetic 400 may be less costly and easier to manufacture due to having fewer parts than the prosthetic shown in FIG. 1.

Figure 18:
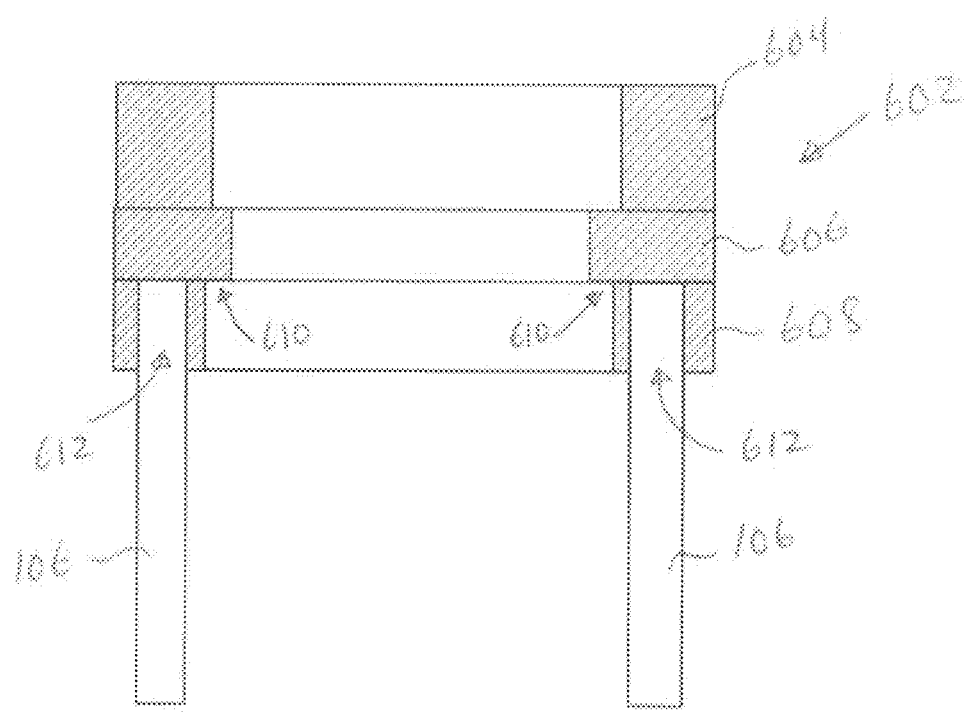
FIG. 18 is one embodiment of a head section of a clamp.

Referring to FIG. 18, according to another embodiment, a head section 602 may be constructed from a plurality of parts. The head section 102 may be constructed from three stacked cylindrical sections 604, 606 and 608 that maybe attached together by a bolts, screws or fasteners. Each cylindrical section may be constructed from a different material to impart a certain property to a region of the head section 102. For example, the cylindrical section 604 may be constructed from titanium or titanium alloy to support the loads associated with engagement of the bolts and/or screws with the pyramid plugs. The cylindrical section 606 may be constructed from a carbon composite material or high-strength steel, and the cylindrical section 608 may be constructed from aluminum, aluminum alloy or carbon composite material. The cylindrical section 606 may have a smaller inner diameter than the cylindrical section 608 to define a stop or ledge 610 for receiving a tube (not shown in FIG. 18) and preventing the tube from passing the cylindrical section 606. The cylindrical section 608 may include a plurality of pin guides 612, into which pins 106 as described herein may be attached. By having the head section being constructed from a plurality of parts, any damage in one portion of the head section does not propagate to the other portions of the head section. For example, a crack in the cylindrical section 604 cannot propagate to the cylindrical section 606 and the cylindrical section 608. As a result, the head section 602 can be safely used by an individual until the entire head section 602 or the damaged part can be replaced. Furthermore, the head section 602 may be lighter than a one piece head section due to the use of different materials for the cylindrical sections 604, 606 and 608. Additionally, the head section 606 may be easier to manufacture than a one piece head section. For example as described in detail above, the one piece head section may include a ledge 122 for stopping further insertion of the tube into the head section. The ledge 122 may be manufactured by machining. As described above, however, the ledge 610 is defined by the cylindrical section 606 having a smaller inner diameter than the cylindrical section 608.

Figure 19:
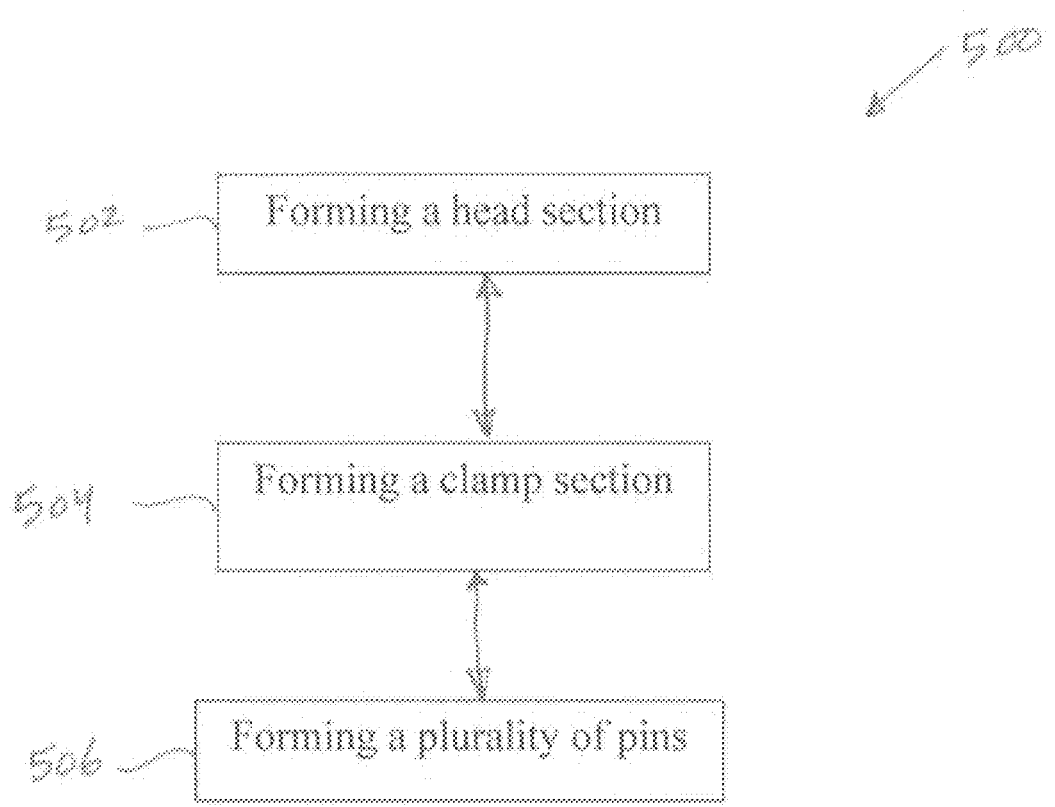
FIG. 19 is a method of manufacturing a clamp according to one embodiment.

Referring to FIG. 19, a process 500 of manufacturing a clamp 100 according to one example is shown. The process 100 includes forming a clamp 100 by forming a head section 102 (block 502), forming a clamp section 104 (block 504), and forming a plurality of pins 106 (block 506). The process 500 may be performed in any order. The clamp 100 can then be assembled as described in detail above. The head section 102, the clamp section 104 and the pins 106 may be manufactured from any material. For example, the head section 102, the clamp section 104 and/or the pins 106 may be made from titanium, titanium alloy, other titanium-based materials, steel, aluminum, aluminum alloy, other metals, metal alloys, plastic, wood, composite materials, or other suitable types of materials. The head section 102, the clamp section 104 and/or the pins 106 may be formed using various processes such as stamping (i.e., punching using a machine press or a stamping press, blanking, embossing, bending, flanging, or coining, casting), injection molding, forging, machining or a combination thereof, other processes used for manufacturing metal, plastic and/or composite parts, and/or other suitable processes. Referring to FIGS. 12-14, each of the discs 206 may be made from titanium, titanium alloy, other titanium-based materials, steel, aluminum, aluminum alloy, other metals, metal alloys, plastic, wood, composite materials, or other suitable types of materials. Additionally, each of the discs 206 may be made from a different material than one or more of the other discs 206 to impart a particular characteristic to the clamp section 104 as discussed in detail above.

As described above, a clamp for a prosthetic may be constructed from a plurality of parts such as a head section, a plurality of pins, and a clamp section. Each of the head section and the clamp section may also be constructed from a plurality of parts. By having the clamp constructed from a plurality of parts, any damage in one portion of the clamp does not propagate to the other portions of the clamp. For example, a crack that may have been present in the head section or may have later developed in the head section may not propagate to the remaining portions of the clamp. As a result, the clamp may be safely used by an individual until the entire clamp or the damaged part can be replaced.

As described in detail above, when the tube is inserted into the clamp 100, the section of the tube that is inside the clamp is visible through the pins. Accordingly, an individual adjusting the length or other characteristics of a prosthesis can visually inspect and adjust the location of the tube because improper location of the tube may cause the weight load of the individual to be unevenly distributed, which may cause the tube to fail.

As described in detail above, any one or both of the head section and the clamp section may be constructed from a plurality of stacked generally cylindrical or disc sections. The multilayered head section and/or the clamp section can better absorb fluctuations and stresses when a prosthesis is in use. Accordingly, the head section and/or the clamp section may have a longer life and/or have a lower risk of failure during use.

The pins separate the head section from the clamp section. Furthermore, the pins are separately loaded from the head section and the clamp section. Accordingly, failure of one pin may not cause the entire clamp section to fail because the remaining pins may burden the load of an individual using the prosthesis. The failed pin can then be replaced without having to replace the entire clamp due to failure.

A clamp or a prosthesis according to the disclosure may be lighter, for example 20 to 30% lighter, than a prosthesis having a one-piece clamp. Accordingly, an individual using the prosthesis may have to use less effort due to the lighter weight of the clamps. Furthermore, the clamp or a prosthesis according to the disclosure may be more flexible as described in detail above so as to be capable of absorbing more bending when the prosthesis is in use. Further yet, because the clamp may be constructed from different materials, more costly materials such as titanium or titanium alloys may be used in the portions of the clamp that experience higher loads (e.g., the head section), and less costly materials such as steel can be used in other portions of the clamp (e.g. the pins). Therefore, the cost of manufacturing a clamp or a prosthesis according to the disclosure may be reduced.

Although a particular order of actions is described above, these actions may be performed in other temporal sequences. For example, two or more actions described above may be performed sequentially, concurrently, or simultaneously. Alternatively, two or more actions may be performed in reversed order. Further, one or more actions described above may not be performed at all. The apparatus, methods, and articles of manufacture described herein are not limited in this regard.

While the invention has been described in connection with various aspects, it will be understood that the invention is capable of further modifications. This application is intended to cover any variations, uses or adaptation of the invention following, in general, the principles of the invention, and including such departures from the present disclosure as come within the known and customary practice within the art to which the invention pertains.

What is claimed is:

1. A prosthetic limb clamp comprising:
a first hollow generally cylindrical body section having an adaptor bore configured to couple to an adaptor of a prosthetic limb and at least one fastener configured to secure the adaptor of the prosthetic limb in the adaptor bore, the first section having a first periphery with a first outer diameter, a first inner diameter defining the adaptor bore, and a first axial space having a first axis;
a second hollow generally cylindrical body section being separate and spaced apart from the first section and having a clamp portion with a clamp bore configured to couple to a pylon, the second section having a second periphery with a second outer diameter, a second inner diameter defining the clamp bore, and second axial space having a second axis, the clamp portion being moveable from an open position wherein the pylon is movable in the clamp bore to a closed position wherein the pylon is secured to the clamp portion; and
a plurality of rigid pins extending between the first section and the second section and connecting the first section to the second section, each pin having a first end connected to the first periphery of the first section and a second end opposite to the first end and the second end is connected to the second periphery of the second section;
a plurality of second pin bores in the second cylindrical body section, wherein each second pin bore is configured to receive the second end of one of the plurality of pins, and the portions of the second cylindrical body section that include the second pin bores extend past the second outer diameter to accommodate the second pin bores,
wherein the plurality of pins define a perimeter for an axial open space between and through the first section and the second section.

2. The clamp of claim 1, wherein the adaptor bore of the first section and the clamp bore of the second section are coaxial, and wherein the pins are located outside of the adaptor bore and the clamp bore, and the pins extend in the same direction as the first axis of the first section and the second axis of the second section.

3. The clamp of claim 1, wherein the first section comprises a generally cylindrical body having a plurality of pin bores extending through the cylindrical body, wherein each pin bore is configured to receive an end portion of one of the plurality of pins.

4. A prosthetic limb clamp comprising:
a first section having a first outer diameter, a first inner diameter defining an adaptor bore configured to receive an adaptor of a prosthetic limb, and a fastener configured to secure the adaptor of a prosthetic limb in the bore of the first section;
a second cylindrical section separate from the first section and the second cylindrical section having a second outer diameter, a clamp portion, and a second inner diameter defining a cylindrical clamp bore configured to receive a pylon of the prosthetic limb, the clamp portion being moveable from an open position wherein the pylon is movable in the clamp bore to a closed position wherein the pylon is secured to the clamp portion;
a plurality of rigid pins connecting the first section to the second section, each pin having a first end connected to the first section and a second end opposite to the first end connected to the second section;
a plurality of second pin bores in the second cylindrical section, wherein each second pin bore is configured to receive the second end portion of one of the plurality of pins, and the portions of the second cylindrical body section that include the second pin bores extend past the second outer diameter of the second cylindrical section to accommodate the second pin bores.

5. The clamp of claim 4, wherein the first section comprises a generally cylindrical body having a plurality of first pin bores extending through the cylindrical body of the first section, wherein each first pin bore is configured to receive the first end portion of one of the plurality of pins; and the portions of the first cylindrical body section that include the first pin bores extend past the second outer diameter of the second cylindrical section to accommodate the second pin bores.

6. The clamp of claim 4, wherein the plurality of pins are composed of a material from the group consisting of: titanium, titanium alloys, and steel.

7. The clamp of claim 4, wherein the plurality of pins are straight.

8. The clamp of claim 4, wherein first section has a first periphery; the second section has a second periphery; and the first periphery and the second periphery defining a perimeter for an axial open space between and through the first section and second section.

9. A prosthetic limb clamp comprising:
a first section having a first outer diameter, a first inner diameter defining a first adaptor bore configured to receive an adaptor of a prosthetic limb, and a fastener configured to secure the adaptor in the bore of the first section;

a second section separate from the first section and the second section having a second outer diameter, a clamp portion, and a second inner diameter defining a second clamp bore configured to receive a pylon, the clamp portion being moveable from an open position wherein the pylon is movable in the clamp bore to a closed position wherein the pylon is secured to the clamp portion;

a plurality of rigid pins connecting the first section to the second section, each pin having a first end connected to the first section and a second end opposite to the first end connected to the second section;

a plurality of second pin bores in the second cylindrical section, wherein each second pin bore is configured to receive the second end portion of one of the plurality of pins, and the portions of the second cylindrical body section that include the second pin bores extend past the second outer diameter of the second cylindrical section to accommodate the second pin bores.

10. The clamp of claim 9, wherein the first section further having a cupped rim.

11. The clamp of claim 9, wherein the plurality of pins are composed of a material from the group consisting of: titanium, titanium alloys, and steel.

12. The clamp of claim 9, wherein the plurality of pins extend in the same direction as a first axis of the first bore of the first section and a second axis of the second bore of the second section; wherein the plurality of pins define a perimeter for an axial open space between and through the first section and second section.

13. The clamp of claim 9, wherein first section has a first periphery; the second section has a second periphery; and the first periphery and the second periphery define a perimeter for an axial open space between and through the first section and second section.

14. The clamp of claim 9, further comprising a plurality of first pin bores in the first cylindrical section, wherein each first pin bore is configured to receive the first end portion of one of the plurality of pins, and the portions of the first cylindrical body section that include the first pin bores extend past the first outer diameter to accommodate the first pin bores.

* * * * *